(12) United States Patent
Buckman, Jr. et al.

(10) Patent No.: US 8,247,728 B2
(45) Date of Patent: Aug. 21, 2012

(54) APPARATUS AND METHOD FOR BONDING REFRACTORY METALS

(75) Inventors: Raymond W. Buckman, Jr., Pittsburgh, PA (US); Udayan Patel, San Jose, CA (US)

(73) Assignee: Icon Medical Corp., Atlanta, GA (US)

( * ) Notice: Subject to any disclaimer, the term of this patent is extended or adjusted under 35 U.S.C. 154(b) by 224 days.

(21) Appl. No.: 12/675,907

(22) PCT Filed: Sep. 5, 2008

(86) PCT No.: PCT/US2008/075434
§ 371 (c)(1),
(2), (4) Date: Aug. 3, 2010

(87) PCT Pub. No.: WO2009/033045
PCT Pub. Date: Mar. 12, 2009

(65) Prior Publication Data
US 2010/0299910 A1   Dec. 2, 2010

Related U.S. Application Data

(60) Provisional application No. 60/967,884, filed on Sep. 7, 2007.

(51) Int. Cl.
*B23K 11/16* (2006.01)

(52) U.S. Cl. ...... 219/56.1; 219/56.22; 219/58; 219/61.5

(58) Field of Classification Search ............... 219/56.1, 219/56.22, 58, 61.5
See application file for complete search history.

(56) References Cited

U.S. PATENT DOCUMENTS

| | | | |
|---|---|---|---|
| 3,170,234 A | 2/1965 | Tarr | |
| 6,596,411 B2 * | 7/2003 | Feng et al. | 428/637 |
| 2006/0200224 A1 | 9/2006 | Furst | |
| 2006/0200225 A1 | 9/2006 | Furst | |
| 2006/0249556 A1 | 11/2006 | Subramanian et al. | |
| 2006/0264914 A1 | 11/2006 | Furst | |
| 2007/0077163 A1 | 4/2007 | Furst | |

* cited by examiner

*Primary Examiner* — Minh-Loan T Tran
(74) *Attorney, Agent, or Firm* — Fay Sharpe, LLP; Brian E. Turung

(57) ABSTRACT

An apparatus and method of bonding refractory metal alloys together by use of a modified clamping arrangement.

29 Claims, 3 Drawing Sheets

APPARATUS AND METHOD FOR BONDING REFRACTORY METALS

The present invention claims priority on PCT Application Serial No. PCT/US 08/75434 filed Sep. 5, 2008, which in turn claims priority on U.S. Provisional Application Ser. No. 60/967,884 filed Sep. 7, 2007 entitled "Stents made of Nuloy and Method of Making the Same," which is incorporated herein by reference.

The invention relates to an apparatus and method for bonding metals together, more particularly to an apparatus and method for bonding refractory metals together, even more particularly to an apparatus and method for bonding refractory metals together to at least partially form a medical device, and still even more particularly to an apparatus and method for bonding molybdenum alloy or tantalum alloy components together to at least partially form a medical device.

BACKGROUND OF THE INVENTION

Medical treatment of various illnesses or diseases commonly includes the use of one or more medical devices. Two types of medical devices that are commonly used to repair various types of body passageways are an expandable graft or stent, or a surgical graft. These devices have been implanted in various areas of the mammalian anatomy. One purpose of a stent is to open a blocked or partially blocked body passageway. Various physical attributes of a stent can contribute directly to the success rate of the device. These physical attributes include radiopacity, hoop strength, radial force, thickness of the metal, dimensions of the metal and the like. Cobalt and chromium alloy and stainless steels are commonly used to form stents. These materials are commonly used since such materials have a known history of safety, effectiveness and biocompatibility. These materials however, have limited physical performance characteristics as to size, strength, weight, bendability, biostability and radiopacity. It is believed that the use of refractory metal alloys such as molybdenum alloys can be used to form medical devices such as stents which have superior properties to medical devices formed from more traditional alloys such as nickel alloys and stainless steel. Non-limiting examples of such refractory metal alloys are disclosed in United States Patent Publication Nos. 2006/0200225; 2006/0200224; 2006/0264914; and 2007/0077163, all of which are incorporated herein by reference.

Although refractory metal alloys can be desirable to form medical devices, it is difficult to bond such metals together to form medical devices. The bonding equipment used to form the bond between the refractory metal alloy materials is commonly subjected to high temperatures and/or pressures, thus resulting in damage to the bonding equipment.

In view of the current state of the art, there is a need for an improved apparatus and method for forming a bond between refractory metal alloys that resists damage during the formation of such a bond.

SUMMARY OF THE INVENTION

The present invention is directed to the bonding together of refractory metal alloys, and more particularly to the bonding together of refractory metal alloys to at least partially form a medical device. The present invention is also directed to an improvement in or relating to diffusion bonding and/or radiation welding (e.g., laser welding, electron beam welding, etc.) of refractory metal alloys. Although the invention will be described with particular reference to devices that are at least partially formed of refractory metal alloys, it will be appreciated that the novel apparatus for bonding and method of bonding can be successfully used to bond together other types of materials (e.g., stainless steel, nickel-titanium alloy, thermoplastic materials, thermoset plastics, composite materials, etc.). Diffusion bonding occurs when two mating surfaces are pressed together under temperature, time and pressure conditions to allow the interchange of atoms across the interface between the two mating surfaces. Generally, the mating surfaces should be clean and the variables of temperature, pressure and time are closely controlled so that the necessary interchange of atoms is achieved during the bonding process. Refractory metals such as alloys of tungsten, molybdenum, niobium, tantalum, iridium, zirconium, and/or rhenium are believed to have superior physical properties for use in various types of medical devices. However, these refractory metals required very high temperatures and/or pressures to cause such materials to be bonded together. Generally, during the bonding process, clamping arrangements are used to secure and force the refractory metal alloy components together to facilitate in the bonding of the refractory metal alloy components. While the refractory metal alloy components are pressed together, heat is applied to the refractory metal alloy components to complete the bonding process. The heat and pressure that the clamping arrangements are exposed to during the bonding process for the refractory metal alloy components typically results in the clamping components to bend, warp or otherwise become damaged thereby resulting in the failure of the formation of a proper and/or desired bond between the refractory metal alloy components. The present invention is directed to an apparatus and method to overcome this problem and to ensure that a desired bond is formed between the refractory metal alloy components.

In one non-limiting aspect of the present invention, there is provided a novel clamping arrangement that is used to clamp or secure together two or more refractory metal alloy components and to position such two or more refractory metal alloy components together during a bonding process. This novel clamping arrangement is designed to be formed of materials that resist warping, bending, melting and/or the like during the bonding of two or more refractory metal alloy components. Typically, during a bonding process, one or more clamping components are secured to a portion of a refractory metal alloy component and then move the refractory metal alloy component toward another refractory metal alloy component thereby creating a high contact pressure or bonding pressure between the two refractory metal alloy components. Heat is typically applied to the region of contact between the two refractory metal alloy components so as to complete the bonding process between the two refractory metal alloy components. The source of heat is typically applied locally on and/or about the contact location of the two refractory metal alloy components. The source of heat is generally a laser or an electron beam; however, other or additional heat sources can be used (e.g., electric arc welder, ultrasonic welder, etc.) when manufacturing various types of devices such as, but not limited to medical devices, repeated bonding sequences are required to form the device that is at least partially form of refractory metal alloy components. For instance, when a medical device such as a stent is formed from refractory metal alloy components, there can be 10-1000 or more bonding sites that are required to create the stent. Exposure of prior art clamping components to repeated high temperatures and pressures has consistently resulted in rapid failure of such clamping components due to warping, bending and/or melting of such clamping components. The novel clamping arrangement of the present invention is at least partially formed of a tungsten containing material that overcomes these past problems of prior art clamping components.

In another and/or alternative non-limiting aspect of the present invention, the novel clamping arrangement of the present invention includes the use of a tungsten containing material that includes a majority weight percent tungsten and one or more additives. Such additives include additives selected from the group of rhenium, hafnium carbide, oxide of thorium, and/or oxide of lanthanum. During a bonding process, it is necessary to hold or clamp two pieces of a device under pressure against each other. The clamping arrangement should not deform or stick or meld with the pieces being bonded together at the applied pressure and bonding temperature. Tungsten is known as a hard material and can withstand deformation at high temperatures and pressure. The melting point of tungsten is about 3410° C. If a device such as, but not limited to, a stent is made from stainless steel wire or an M25 alloy wire (beryllium copper alloy), then a clamping arrangement formed of pure tungsten can be successfully used to stent components together without concern of the tungsten clamping arrangement deforming, melting, sticking and/or bonding with the pieces of the stent during the bonding process. However, it has been found that a clamping arrangement formed of pure tungsten may not always resist the conditions for bonding together metal components of a device when the device is formed of metals from Group V and VI of the Periodic Table (e.g., vanadium, niobium, tantalum, molybdenum, tungsten, etc.). For instance, a metal component formed of Mo47.7Re has a melting point of more than 2000° C. Tungsten clamping arrangements, when exposed to such temperatures and high pressures during the bonding of metal components formed of metals from Group V and VI has a tendency to warp and/or bend after repeated bonding cycles. To overcome this deficiency of pure tungsten clamping arrangements, the novel clamping arrangement of the present invention is formed of a majority weight percent tungsten and one or more additives. In one non-limiting embodiment of the invention, the portion of the clamping arrangement that is used to secure to a component of a device during a bonding process includes at least about 90 weight percent tungsten and at least about 0.4 weight percent and up to about 10 weight percent hafnium carbide, oxide of thorium and/or oxide of lanthanum. In one non-limiting aspect of this embodiment, the portion of the clamping arrangement that is used to secure to a component of a device during a bonding process includes at least about 95 weight percent tungsten and at least about 0.5 weight percent and less than about 4 weight percent hafnium carbide, oxide of thorium and/or oxide of lanthanum. In another non-limiting aspect of this embodiment, the portion of the clamping arrangement that is used to secure to a component of a device during a bonding process includes at least about 95 weight percent tungsten and about 0.5-3.5 weight percent oxide of thorium, and more particularly about 2-2.5 weight percent oxide of thorium. In still another non-limiting aspect of this embodiment, the portion of the clamping arrangement that is used to secure to a component of a device during a bonding process includes at least about 95 weight percent tungsten and at least about 0.5 weight percent and less than about 4 weight percent oxide of lanthanum. In yet another non-limiting aspect of this embodiment, the portion of the clamping arrangement that is used to secure to a component of a device during a bonding process includes at least about 95 weight percent tungsten and about 0.5-3.5 weight percent oxide of lanthanum, and more particularly about 2-2.5 weight percent oxide of lanthanum. In still yet another non-limiting aspect of this embodiment, the portion of the clamping arrangement that is used to secure to a component of a device during a bonding process includes at least about 95 weight percent tungsten and about 0.5-3.5 weight percent hafnium carbide, and more particularly about 0.5-1.5 weight percent hafnium carbide. In another non-limiting aspect of this embodiment, the portion of the clamping arrangement that is used to secure to a component of a device during a bonding process includes at least about 95 weight percent tungsten and at least about 0.5 weight percent and less than about 4 weight percent of at least two compounds selected from the group of hafnium carbide, oxide of thorium and oxide of lanthanum. In another non-limiting aspect of this embodiment, the portion of the clamping arrangement that is used to secure to a component of a device during a bonding process includes at least about 95 weight percent tungsten and about 0.5-3.5 weight percent at least two compounds selected from the group of hafnium carbide, oxide of thorium and oxide of lanthanum, and more particularly about 2-2.5 weight percent at least two compounds selected from the group of hafnium carbide, oxide of thorium and oxide of lanthanum. In still another non-limiting aspect of this embodiment, the portion of the clamping arrangement that is used to secure to a component of a device during a bonding process includes at least about 95 weight percent tungsten and at least about 0.5 weight percent and up to about 2 weight percent oxide of thorium and at least about 0.5 weight percent and up to about 2 weight percent oxide of lanthanum, more particularly about 0.5-1.5 weight percent oxide of thorium and about 0.5-1.5 weight percent oxide of lanthanum, and still more particularly about 0.5-1 weight percent oxide of thorium and about 0.5-1 weight percent oxide of lanthanum. In yet another non-limiting embodiment of the invention, the portion of the clamping arrangement that is used to secure to a component of a device during a bonding process includes at least about 70 weight percent tungsten and at least about 10 weight percent rhenium. In one non-limiting aspect of this embodiment, the portion of the clamping arrangement that is used to secure to a component of a device during a bonding process includes at least about 72 weight percent tungsten and at least about 15 weight percent rhenium. In another non-limiting aspect of this embodiment, the portion of the clamping arrangement that is used to secure to a component of a device during a bonding process includes at least about 72 weight percent tungsten and about 15-28 weight percent rhenium.

In still another non-limiting aspect of this embodiment, the portion of the clamping arrangement that is used to secure to a component of a device during a bonding process includes at least about 72 weight percent tungsten, at least about 15 weight percent rhenium and at least one additional additive. Such additional additive includes, but is not limited to, hafnium carbide, oxide of thorium and/or oxide of lanthanum. In still yet another non-limiting aspect of this embodiment, the portion of the clamping arrangement that is used to secure to a component of a device during a bonding process includes at least about 72 weight percent tungsten, at least about 15 weight percent rhenium and about 0.5-2 weight percent oxide of thorium, about 0.5-2 weight percent oxide of lanthanum, and/or about 0.5-1.5 weight percent hafnium carbide. In another non-limiting aspect of this embodiment, the portion of the clamping arrangement that is used to secure to a component of a device during a bonding process includes at least about 72 weight percent tungsten, about 15-26 weight percent rhenium and about 0.5-1 weight percent oxide of thorium, about 0.5-1 weight percent oxide of lanthanum, and/or about 0.5-1 weight percent hafnium carbide. The addition of rhenium, hafnium carbide, oxide of thorium and/or oxide of lanthanum in controlled amounts has been found to not significantly reduce the melting temperature of the modified tungsten material and has been found to increase the tensile strength and ductility of the modified tungsten as compared to pure tungsten, thereby enabling the modified tungsten to better resist bending and warping during the bonding process for refractory metal alloys.

In still another and/or alternative non-limiting aspect of the present invention, the novel clamping arrangement of the present invention can be at least partially coated with a material to reduce the incidence of sticking during the bonding of components of a device; however, this is not required. During certain bonding procedures that involve high temperatures and pressures, the portion of the clamping arrangement that is used to secure to a component of a device during the bonding process can stick to the components of a device during or after completion of the bonding process. Such sticking can result in damage to the device when the clamping arrangement is separated from the components of a device after the bonding process is completed. In order to reduce the incidence of sticking during and after a bonding process, the portion of the clamping arrangement that is used to secure to a component of a device during the bonding process can be coated with a metal oxide layer. One such metal oxide layer can be at least partially formed of an oxide of titanium, zirconium and/or hafnium. The metal oxide layer is believed to resist the incidence of sticking by reducing the heat transfer from the components of the device being bonded to the tungsten clamping arrangement. As can be appreciated, the metal oxide layer can reduce the incidence of sticking by other or additional mechanisms. The thickness of the metal oxide layer is generally at least about 5 microns, typically at least about 10 microns, more typically about 12-200 microns, and even more typically about 12-150 microns. The oxide layer, when used, can be applied to the clamping arrangement by any number of process. Generally, the oxide layer is applied by first applying a thin metal layer on the clamping arrangement by one or more processes (e.g., vacuum vapor deposition, plasma spraying, electroplating, etc.) and then oxidizing the thin metal layer.

In yet another and/or alternative non-limiting aspect of the present invention, there is provided a process for forming a medical device such as a stent by use of a bonding process. The stent is generally at least partially formed from a wire, ribbon, hollow tube or other geometrically shaped material. The cross-sectional shape of the material used to form the stent can have a variety of shapes (e.g., round, oval, rectangular, square, hollow and the like). Additionally, the material used to form the stent can be formed into various shapes and/or patterns (e.g., a repeating sinusoidal wave pattern, etc.). In one non-limiting arrangement, the ends of the pieces of material used to form the stent can be bonded together (e.g., diffusion bonded, welded, soldered, adhesively connected, etc.) to form a ring. In one non-limiting embodiment, the stent can be made up of plastically deformable material or a superelastic material. The plastically deformable material or superelastic material, when used, typically has a minimal recoil after being deformed. This minimum recoil property is particularly important when the stent is collapsed over an angioplasty balloon. After the stent is collapsed over the angioplasty balloon, the stent should retain its shape so that it can grip the angioplasty balloon tightly and not fall off when being inserted into a body passageway. After the stent is positioned and expanded in a body passageway, the stent should stay in the exact or substantially exact expanded diameter to prevent reduction of the cross-sectional area of the expanded body passageway. Two such materials that can be used for a stent that has such desired properties are a stent formed of a molybdenum and rhenium alloy or tantalum and tungsten alloy. During the formation of the stent, pressure and heat are typically applied to one or more components of the stent to form a plurality of bonds in the stent. When the stent is formed from a plurality of rings, an energy source is generally directed to the connection points on the ring so as to form a connection or bond between at least one other ring. Non-limiting examples of energy sources include the use of electric arc welding, vacuum arc welding, laser welding, electron beam welding, ultrasonic welding, etc. During the bonding process, the bond can be formed in an inert environment; however, this is not required. When an inert environment is used, the inert environment can be achieved by a variety of arrangements (e.g., vacuum, use of inert gas, etc.). In one non-limiting arrangement, the inert environment, when used, can be created by either by forcing inert gases to the bonding site before, during and/or after the bonding process or forming an enclosure for the bonding region and inserting an inert gas in the bonding region so that the bonding process is carried out in an inert environment. If an enclosure is used for the inert environment, such enclosure can include a bleed port to enable inert gas to flow into and/or out of the enclosure; however, this is not required. When a bleed port is used, the bleed port can be used to enable cooled or cooler inert gas to be inserted into the enclosure so as to at least partially control the temperature in the enclosure; however, this is not required. Any number of inert gasses or combinations of inert gasses can be used during the bonding process. When the stent is formed of refractory metals, a reducing atmosphere is favorable. Such a reducing atmosphere can include, but is not limited to, hydrogen, and in argon environment. During the bonding process, the components of the stent are held together under pressure against each other. The clamping arrangement that is used to hold the components of the stent together during the bonding process should not deform, stick or meld with the stent components at the applied pressures and temperatures during the bonding process. Pure tungsten can be used to form the portion of the clamping arrangement that holds the components of the stent together during the bonding process. As can be appreciated, other portions of the clamping arrangement can also include tungsten; however, this is not required. Tungsten is a hard material that can withstand deformation at high temperatures and pressures. When the stent is made from stainless steel wire or an M25 alloy wire, pure tungsten can be used to form the portion of the clamping arrangement that holds the wire of the stent together during the bonding process. Generally, the clamping arrangement includes and/or is formed of a material having a higher melting temperature and/or is a harder material that the wire of the stent; however, this is not required. The use of a clamping arrangement that includes and/or is formed of a material having a higher melting temperature and/or being of a harder material that the wire of the stent facilitates in the clamping arrangement resisting deformation during the bonding process. When the stent is formed of refractory metal alloys, pure tungsten may not be able to resist the conditions for bonding such components of the stent together without warping, bending, melting, and/or sticking to the components of the stent during and/or after the bonding process. For example, a wire that is used to form a stent which is made of an alloy of molybdenum and rhenium has a melting that exceeds 2000° C. High pressures can be used during the bonding process to create a bond below the melting point of the molybdenum and rhenium alloy; however, at such temperatures and pressures, the clamping arrangement formed of pure tungsten has a tendency to deform and/or stick to the stent components, especially after repeated bonding processes during the formation of the stent. When bonding refractory metal alloys, the portion of the clamping arrangement that holds the wire of the stent together during the bonding process can be formed of a majority of tungsten and one or more additives selected from the group of rhenium, oxide of thorium and/or oxide of lanthanum. The surfaces of the portion of the clamping arrangement that holds and contacts the wire of the stent during the bonding process can include an oxide layer; however, this is not required. The oxide layer, when used, can facilitate in reducing the incidence of sticking between the clamping arrangement and the wire of the stent during the bond process, and/or reduce heat transfer to the clamping arrangement during the bonding process so as to reduce the incidence of damage to the clamping arrangement that is caused by heat during the bonding process. Non-limiting examples of metal oxides that can be coated on tungsten or tungsten that includes one or more additives include oxides of titanium, zirconium and/or hafnium. The thickness of the metal oxide layer, when used, is generally at least about 10 microns, and typically about 12-175 microns.

One non-limiting object of the present invention is to provide an improved apparatus and method for bonding materials together.

Another and/or alternative non-limiting of the present invention is to provide an improved apparatus and method for bonding to refractory materials together.

Still another and/or alternative non-limiting object of the present invention is to provide an improved apparatus and method for bonding materials together that includes the use of a clamping arrangement that holds together materials that are to be bonded together, and which clamping arrangement resists warping, bending and/or melting before, during and/or after a bonding process.

Yet another and/or alternative non-limiting object of the present invention is to provide an improved apparatus and method for bonding materials together that includes the use of a clamping arrangement that holds together materials that are to be bonded together, and which clamping arrangement resists sticking to materials that are to be bonded together before, during and/or after a bonding process.

Still yet another and/or alternative non-limiting object of the present invention is to provide an improved apparatus and method for bonding materials together that includes the use of novel tungsten containing composition that is used to together materials that are to be bonded together.

Another and/or alternative non-limiting object of the present invention is to provide an improved apparatus and method for bonding materials together that includes the use of a clamping arrangement that holds together materials that are to be bonded together, and which clamping arrangement includes a metal oxide layer.

Still another and/or alternative non-limiting object of the present invention is to provide an improved apparatus and method for bonding materials together that includes the use of an inert environment during the bonding process.

Yet another and/or alternative non-limiting object of the present invention is to provide an improved apparatus and method for bonding materials together that maintains at least a minimum ratio of temperature to pressure during the bonding process to form a desired bond between the materials to be bonded together.

Still yet another and/or alternative non-limiting object of the present invention is to provide an improved apparatus and method for bonding materials together materials that are used to form medical devices such as, but not limited to, stents.

These and other advantages will become apparent to those skilled in the art upon the reading and following of this description taken together with the accompanying drawings.

DETAILED DESCRIPTION OF THE INVENTION

Figure 1:
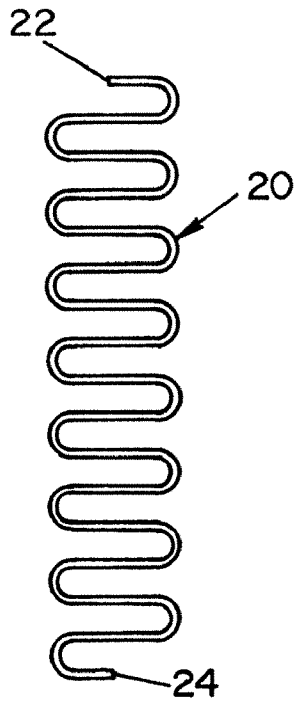
FIG. 1 is a top view of a wire bent into serpentine form.
Figure 2:
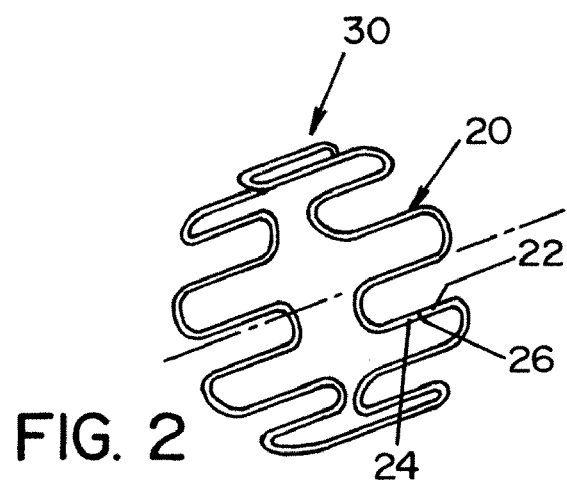
FIGS. 2 and 2A are elevation views of the wire of FIG. 1 bonded at its ends and formed into a ring.
Figure 3:
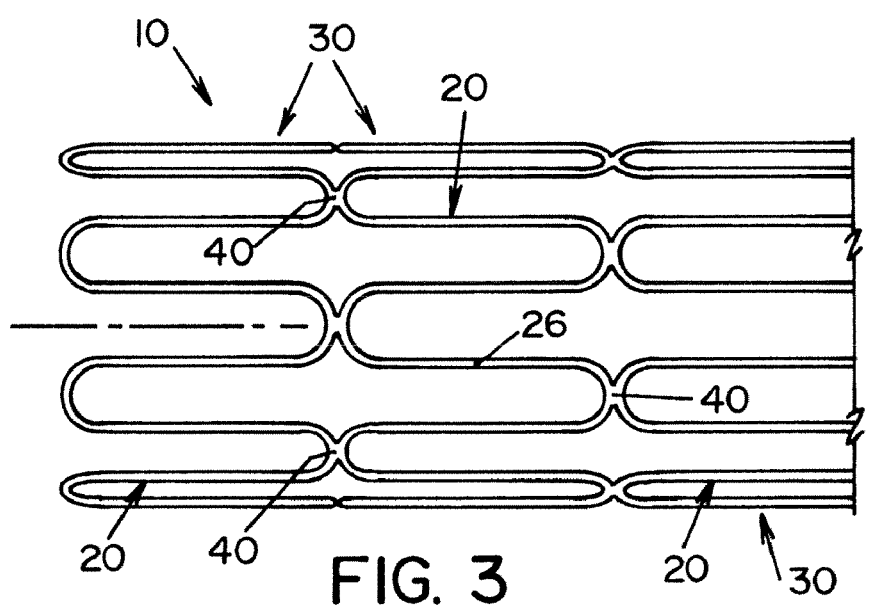
FIG. 3 is a side view of a stent that is formed from a plurality of rings of FIG. 2.

Referring now to the drawings wherein the showings are for the purpose of illustrating non-limiting embodiments of the invention only and not for the purpose of limiting the same, FIGS. 1-3 illustrate a non-limiting arrangement for a stent 10 that can be formed by the bonding process of the present invention. FIG. 1 illustrates a wire material 20 that has been bent into a serpentine pattern. As can be appreciated, the pattern of the wire can have a shape other than a serpentine pattern. The cross-section of the wire, not shown, can be circular, oval, rectangular, square, etc. The wire can be a solid wire or a hollow wire.

Figure 2A:
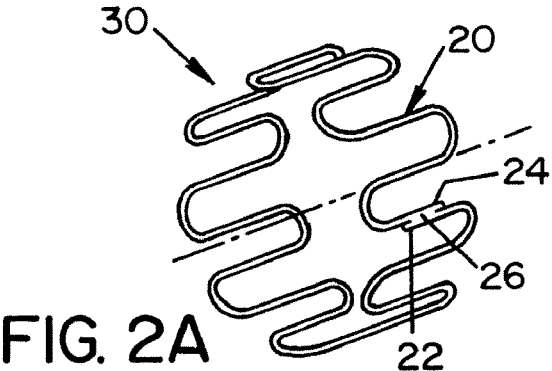

FIGS. 2 and 2A illustrate the formation of a ring section 30 by bending the two ends 22, 24 of wire 20 together and then connected together ends 22, 24. As illustrated in FIG. 2, the bond is formed directly between the two ends so that the two ends are aligned with one another. As illustrated in FIG. 2A, the bond 26 formed between ends 22, 24 is located adjacent to ends 22, 24. As can be appreciated, ends 22, 24 can be aligned together in other manners prior to forming the bond between the two ends. Bond 26 can be formed by any number of means depending on the type of wire material and/or the type of bond required. Non-limiting examples of bonding methods that can be used include diffusion bonding, laser bonding, electric arc welding, ultrasonic welding, adhesive, etc. Indeed, the bonding process of the present invention that will be described in more detail below can also be used to connect together ends 22, 24 of wire 20. As can also be appreciated, the ring section 30 can be formed by other processes (e.g., cutting a tube of material into ring sections and then stamping the desired pattern into the ring sections, etc.). As can also be appreciated, prior to, during, or after the ring section has been formed, the ring section or wire used to form the ring section can be polished to form a round shape, square shape with or without chamfered edges, rectangular shape with or without chamfered edges, oval shape, etc.; however, this is not required.

Many different materials can be used to form wire 20. As disclosed in United States Patent Publication Nos. 2006/0200225; 2006/0200224; 2006/0264914; and 2007/0077163, certain types of refractory metal alloys can be used to form medical devices such as, but not limited to, stents that have superior properties to other types of stents. Such properties of these refractory metal alloys are disclosed in detail in United States Patent Publication Nos. 2006/0200225; 2006/0200224; 2006/0264914; and 2007/0077163, thus will not be repeated herein. Non-limiting refractory metal alloys that can be used to form wire 20 are set forth in the below examples.

| | Wt. % | | | | |
|---|---|---|---|---|---|
| Metal | Ex. 1 | Ex. 2 | Ex. 3 | Ex. 4 | Ex. 5 |
| Mo | 50-60% | 50-55% | 51-54% | 52.5-55.5% | 50.5-52.4% |
| Nb | ≦5% | ≦5% | ≦5% | ≦5% | ≦5% |
| Rare Earth Metal | ≦4% | ≦4% | ≦4% | ≦4% | ≦4% |
| Re | 40-50% | 45-50% | 46-49% | 44.5-47.5% | 47.6-49.5% |
| Ta | ≦3% | ≦3% | ≦3% | ≦3% | ≦3% |
| Ti | ≦1% | ≦1% | ≦1% | ≦1% | ≦1% |
| W | ≦3% | ≦3% | ≦3% | ≦3% | ≦3% |
| Y | ≦0.1% | ≦0.1% | ≦0.1% | ≦0.1% | ≦0.1% |
| Zn | ≦0.1% | ≦0.1% | ≦0.1% | ≦0.1% | ≦0.1% |
| Zr | ≦2% | ≦2% | ≦2% | ≦2% | ≦2% |

| | Wt. % | | | |
|---|---|---|---|---|
| Metal | Ex. 6 | Ex. 7 | Ex. 8 | Ex.9 |
| Ca | ≦1% | ≦1% | ≦1% | ≦1% |
| Mg | ≦1% | ≦1% | ≦1% | ≦1% |
| Mo | ≦1% | ≦1% | ≦1% | ≦1% |
| Rare Earth Metal | ≦1% | ≦1% | ≦1% | ≦1% |
| Re | ≦6% | ≦6% | ≦6% | ≦6% |
| Ta | 85-96% | 10-90% | 95-98% | 90.5-98% |
| W | 4-15% | 10-90% | 2-5% | 2-9.5% |
| Y | ≦1% | ≦1% | ≦1% | ≦1% |
| Zn | ≦1% | ≦1% | ≦1% | ≦1% |
| Zr | ≦1% | ≦1% | ≦1% | ≦1% |

The above examples of refractory metal alloys are non-limiting. Additional non-limiting examples are disclosed in United States Patent Publication Nos. 2006/0200225; 2006/0200224; 2006/0264914; and 2007/0077163, all of which are incorporated herein by reference. The diameter or cross-sectional area of wire 20 can be very small when the wire is used to form a stent. Non-limiting examples of the diameter or cross-sectional area of wire 20 that can be bonded by the apparatus and method of the present inventions are disclosed in United States Patent Publication Nos. 2006/0200225; 2006/0200224; 2006/0264914; and 2007/0077163, all of which are incorporated herein by reference.

As illustrated in FIG. 3, a portion of stent 10 is illustrated as formed by a plurality of ring sections 30 connected together by a plurality of bonds 40 formed by the bonding process of the present invention.

Figure 4:
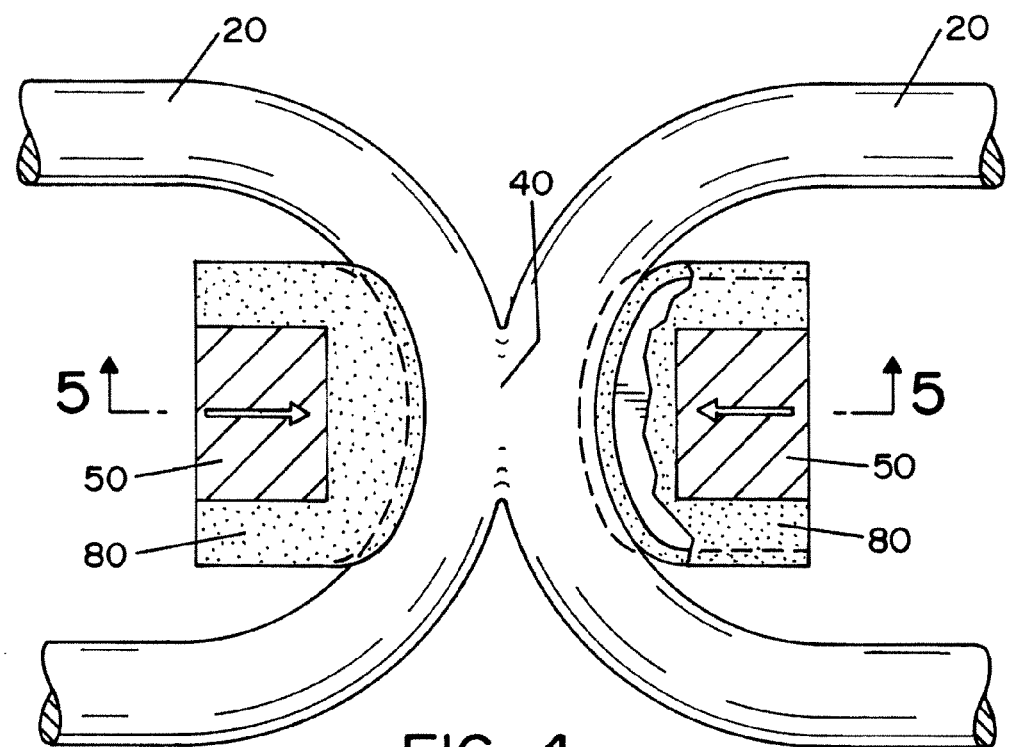
FIG. 4 is an enlarged side view illustrating the bonding together of a portion of two rings.
Figure 5:
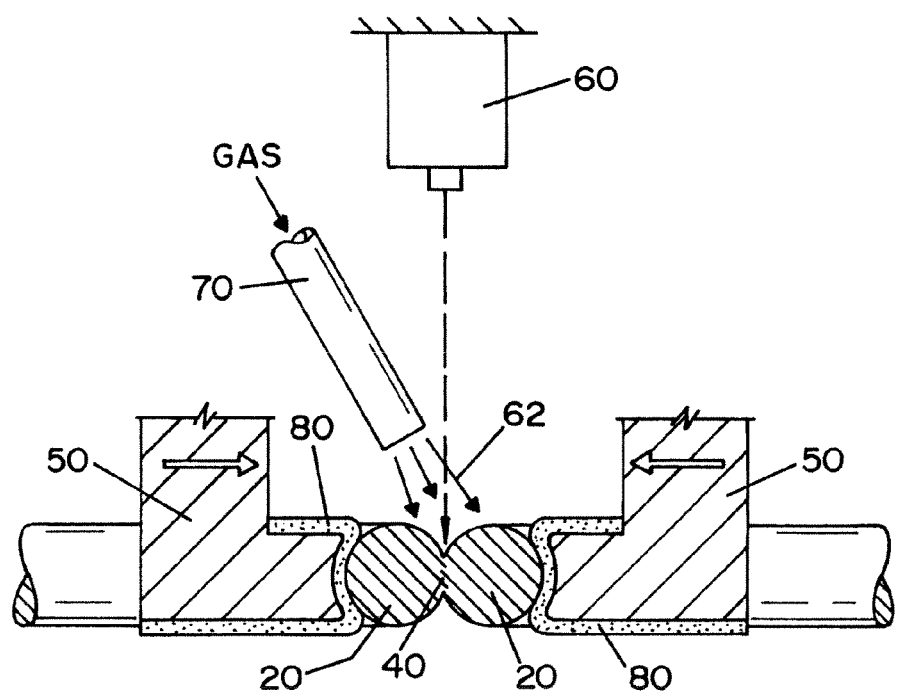
FIG. 5 is a cross-sectional view along line 5-5 of FIG. 4 and illustrating the use of a heat source and protective gas being applied to the bond area; and, FIG. 6 is a pressure and temperature graft illustrating temperature and pressure ratios required to form a good bond between two rings.

Referring now to FIGS. 4-5, there is illustrated an apparatus and method for forming bonds 40 between two wires 20 in accordance with the present invention. The apparatus of forming bond 40 includes a clamping arrangement that includes two clamps 50 that are designed to be releasably secured to a portion wire 20. The two clamps 50 are designed to move wires 20 together as illustrated by the arrows in FIGS. 4 and 5. The clamps can be designed to move wires 20 into contact and apply large amounts of pressure to the two wires to facilitate in forming bond 40. As illustrated in FIG. 5, after wires 20 are brought together, a source of energy 60 applies heat to the region on or about the location that bond 40 is to be formed. The source of energy is typically a laser; however, other or additional sources of energy can be used to form bond 40. Generally bond 40 is formed within a few seconds (e.g., 2-60 seconds, etc.). Bond 40 can be formed in the presence of an inert environment; however, this is not required. As illustrated in FIG. 5, a stream of inert gas 60 from a gas source 70 is directed to the region about bond 40 so as to form an inert environment about bond 40 prior to, during and/or after the forming of bond 40. As can be appreciated, the inert environment can be created by other means. One non-limiting inert gas than can be used is gas containing about 1-10 weight percent hydrogen and the balance argon, and more typically about 3 weight percent hydrogen and the balance argon.

Figure 6:
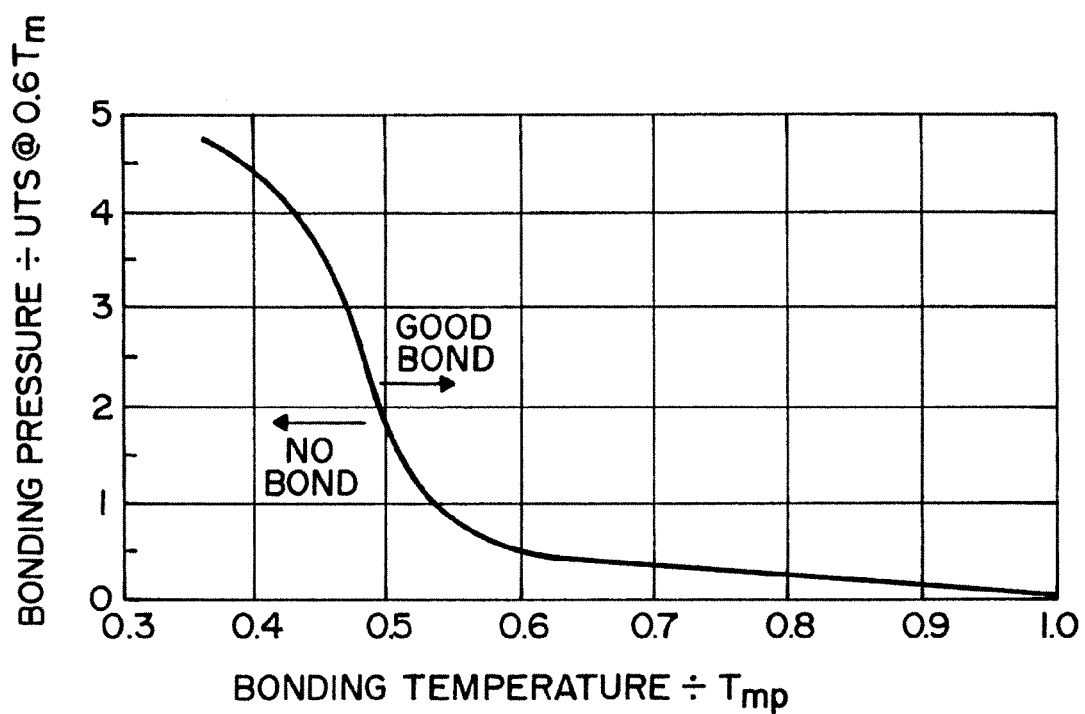

When wires 20 are formed of refractory metal alloys, high temperatures and/or high pressures are required to form a quality bond 40 as illustrated in FIG. 6. Traditional materials used to form clamps 50 have a tendency to bend and warp when forming multiple bonds 40 during the formation of stent 10. In accordance with the present invention, clamps 50 are at least partially formed of a novel tungsten composition that includes a majority weight percent tungsten and one or more additives. The one or more additives generally include an additive selected from the group of rhenium, hafnium carbide, oxide of thorium and/or oxide of lanthanum. Non-limiting examples of the novel tungsten composition is set forth below.

| | Wt. % | | | |
|---|---|---|---|---|
| Component | Ex. 1 | Ex. 2 | Ex. 3 | Ex. 4 |
| W | 95-99.5 | 98-99.5% | 68-85% | 75-85% |
| Re | 0% | 0% | 15-28% | 15-25% |
| ThO$_2$ | ≦2.5% | ≦1% | ≦2% | ≦1% |
| La$_2$O$_3$ | ≦2.5% | ≦1% | ≦2% | ≦1% |
| HfC | ≦2.5% | ≦1% | ≦2% | ≦1% |

The modified tungsten material has a higher tensile strength and ductility as compared to pure tungsten. The improved properties of the modified tungsten material in accordance with the present invention better resist bending and warping when forming bond 40 as compared to pure tungsten. Generally clamps 50 include and/or are formed of a material that has a higher melting temperature and/or is a harder material than wire 20. The use of a clamping arrangement that includes and/or is formed of a material having a higher melting temperature and/or is of a harder material than wire 20 facilitates in the clamping arrangement resisting deformation during the bonding process.

The clamps 50 can include a metal oxide coating 80 as illustrated in FIGS. 4 and 5; however, this is not required. The metal oxide coating 80 is formulated to reduce the incidence of the clamps 50 sticking to wires 20 during and/or after the bonding process. When the metal oxide coating is used, such coating is formed of an oxide of titanium, zirconium or hafnium. The thickness of the metal oxide coating is generally about 10-127 microns.

As illustrated in FIG. 6, a good or desired bond 40 is formed when the proper combination of pressure and temperature are applied to wires 20 during the formation of bond 40. As illustrated in FIG. 6, the higher pressure applied to wires 20, the lower the temperature that is needed to form bond 40. The X-axis of the graph represents a ratio of the bonding temperature used during the formation of bond 40 to the melting temperature of wire 20. The Y-axis represents the bonding pressure used during the formation of bond 40 divided by the ultimate tensile strength (UTS) of wire 20 at a temperature that is 60% of the melting temperature of wire 20. As noted in the graft, the line defining the boundary between the formation of a good bond and a failed bond is generally linear when the ratio of the bonding temperature used during the formation of bond 40 to the melting temperature of wire 20 is about 0.6 to about 1. When the ratio of the bonding temperature used during the formation of bond 40 to the melting temperature of wire 20 is less than about 0.6, the pressure needed to form a good bond increases at a substantial rate, especially once the ratio of the bonding temperature used during the formation of bond 40 to the melting temperature of wire 20 is less than about 0.52. As such, although the graft illustrates that a good bond can be formed when the ratio of the bonding temperature used during the formation of bond 40 to the melting temperature of wire 20 is less than about 0.6, the increase in bonding pressure needed to form bond 40 can result in integrity problems associated with clamp 50 at such high pressures. In practice, bond 40 is formed when the ratio of the bonding temperature used during the formation of bond 40 to the melting temperature of wire 20 is at least about 0.6, and typically about 0.6-0.95, more typically about 0.6-0.9, and even more typically about 0.6-0.8. As illustrated by the graph in FIG. 6, by slightly increasing the bonding pressure between wires 20, the bond temperature can be substantially reduced thereby facilitating in reducing the incidence of warping and/or bending of clamps 50 and/or reducing the incidence of the clamps sticking to wires 20 during and/or after the bonding process. It has been determined that when the ratio of the bonding temperature used during the formation of a bond to the melting temperature of wire is about 0.6 or greater, the slope of the line substantially linear and fits the equation $Y=c-mX$ wherein c is about 1 to 1.4 and generally about 1.2 and m is about 1 to 1.4 and generally about 1.66. By following this pressure and temperature relationship when the ratio of the bonding temperature used during the formation of a bond to the melting temperature of wire is about 0.6 or greater, a high quality bond 40 can be formed by the bonding method of the present invention.

Based on the data from the graph, the needed pressure and temperature can be determined to create a desired bond 40 for a particular material. For instance, if wire 20 was formed of a molybdenum and rhenium alloy that includes about 52.5 weight percent molybdenum and 47.5% rhenium (Mo47.5Re), the melting temperature of such a wire is about 2286° C. and the wire has an UTS at 60% of the melting temperature (i.e., 1372° C.) of about 15 ksi. Based on this information, bond parameters can be set based on the graph. For example, if the bonding temperature of the Mo47.5Re is about 90% of the wire melting temperature (i.e., 2057° C.) which is represented as 0.9 on the X-axis of the graft, the corresponding point on the Y-axis is about 0.15. As such, the minimum bonding pressure during such a bonding process should be at least about 2.25 ksi. In another example, if the bonding temperature of the Mo47.5Re is about 60% of the wire melting temperature (i.e., 1372° C.) which is represented as 0.6 on the X-axis of the graft, the corresponding point on the Y-axis is about 0.5, thus the minimum bonding pressure during such a bonding process should be at least about 7.5 ksi. As can be appreciated, the bonding pressure can be first selected and then the required bonding temperature can be calculated based on the date in the graft.

It will thus be seen that the objects set forth above, among those made apparent from the preceding description, are efficiently attained, and since certain changes may be made in the constructions set forth without departing from the spirit and scope of the invention, it is intended that all matter contained in the above description and shown in the accompanying drawings shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations insofar as they come within the scope of the present invention. It is also to be understood that the following claims are intended to cover all of the generic and specific features of the invention herein described and all statements of the scope of the invention, which, as a matter of language, might be said to fall therebetween.

What is claimed is:

1. A clamping arrangement for use in compressing together two articles so that a welded bond can be formed between the two articles, said two articles formed of refractory metal alloy, said clamping arrangement including a first clamp that is at least partially formed of a tungsten material, said first clamp designed to releasably secure a portion of one of said articles to be bonded and to release from said article after said bond is formed between said two articles, said tungsten material includes a majority weight percent tungsten and at least one additive selected from the group consisting of rhenium, hafnium carbide, an oxide of thorium, an oxide of lanthanum, and mixtures thereof.

2. The clamping arrangement as defined in claim 1, wherein at least a portion of an outer surface of said first clamp includes a metal oxide coating that is designed to contact said article, said metal oxide coating including one or more oxides selected from the group consisting of an oxide of titanium, an oxide of zirconium and an oxide of hafnium.

3. The clamping arrangement as defined in claim 2, wherein said metal oxide coating has a thickness of at least about 10 microns.

4. The clamping arrangement as defined in claim 3, including a second clamp, said second clamp designed to releasably secure a portion of one of said articles to be bonded and to release from said article after said bond is formed between said two articles, said second clamp formed of the same composition as said first clamp.

5. The clamping arrangement as defined in claim 4, wherein at least a portion of an outer surface of said second clamp includes a metal oxide coating that is designed to contact said article, said metal oxide coating including one or more oxides selected from the group consisting of an oxide of titanium, an oxide of zirconium and an oxide of hafnium.

6. The clamping arrangement as defined in claim 5, wherein said tungsten material includes at least 95 weight percent tungsten and one or more additives selected from the group consisting of at least about 0.5 weight percent of an oxide of thorium, at least about 0.5 weight percent of an oxide of lanthanum, and at least about 0.5 weight percent hafnium carbide.

7. The clamping arrangement as defined in claim 6, wherein one or more of said additives is selected from the group consisting of about 0.5-2.5 weight percent of an oxide of thorium, about 0.5-2.5 weight percent of an oxide of lanthanum and about 0.5-2 weight percent of an oxide of thorium.

8. The clamping arrangement as defined in claim 5, wherein said tungsten material includes at least about 10 weight percent rhenium.

9. The clamping arrangement as defined in claim 8, wherein said tungsten material includes about 15-27.5 weight percent rhenium.

10. The clamping arrangement as defined in claim 1, including a second clamp, said second clamp designed to releasably secure a portion of one of said articles to be bonded and to release from said article after said bond is formed between said two articles, said second clamp formed of the same composition as said first clamp.

11. The clamping arrangement as defined in claim 10, wherein at least a portion of an outer surface of said second clamp includes a metal oxide coating that is designed to contact said article, said metal oxide coating including one or more oxides selected from the group consisting of an oxide of titanium, an oxide of zirconium and an oxide of hafnium.

12. The clamping arrangement as defined in claim 1, wherein said tungsten material includes at least 95 weight percent tungsten and one or more additives selected from the group consisting of at least about 0.5 weight percent of an oxide of thorium, at least about 0.5 weight percent of an oxide of lanthanum, and at least about 0.5 weight percent hafnium carbide.

13. The clamping arrangement as defined in claim 12, wherein one or more of said additives is selected from the group consisting of about 0.5-2.5 weight percent of an oxide of thorium, about 0.5-2.5 weight percent of an oxide of lanthanum and about 0.5-2 weight percent of an oxide of thorium.

14. The clamping arrangement as defined in claim 1, wherein said tungsten material includes at least about 10 weight percent rhenium.

15. The clamping arrangement as defined in claim 14, wherein said tungsten material includes about 15-27.5 weight percent rhenium.

16. A method for forming a bond between first and second articles, said two articles formed of refractory metal alloy, said method comprising:
 a) providing a first clamp, said first clamp including a clamping region designed to releasably secure a portion of said first article, said clamping region at least partially formed of a tungsten material, said tungsten material includes a majority weight percent tungsten and one or more additives selected from the group consisting of rhenium, hafnium carbide, an oxide of thorium and an oxide of lanthanum;
 b) releasably securing said first article by said clamping region of said first clamp;
 c) positioning a portion of said first article into contact with a portion of said second article;
 d) applying heat at or near a region wherein said first and second articles are in contact until a bond is formed between said first and second articles; and,
 e) releasing said first article from said clamping region of said first clamp.

17. The method as defined in claim 16, including a second clamp, said second clamp including a clamping region designed to releasably secure a portion of said second article, said clamping region of said second clamp at least partially formed of a tungsten material, said tungsten material includes a majority weight percent tungsten and at least one additive selected from the group consisting of rhenium, an oxide of thorium, an oxide of lanthanum, and mixtures thereof.

18. The method as defined in claim 17, including the step of pressing said first and second articles together by at least one of said clamp during said step of applying heat.

19. The method as defined in claim 18, wherein said bond between said first and second articles is formed by a controlled bonding temperature and a controlled bonding pressure, a selection of said controlled bonding temperature and said controlled bonding pressure is at least partially based on a relationship of $Y=c-mX$, wherein Y is a ratio of said bonding pressure to an ultimate tensile strength of said first and second articles at a temperature of 60% of a melting temperature of said first and second articles, X is a ratio of said bonding temperature to said melting temperature of said first and second articles, c is about 1 to 1.4, and m is about 1 to 1.4.

20. The clamping arrangement as defined in claim 19, wherein at least a portion of an outer surface of said first clamp includes a metal oxide coating that is designed to contact said article, said metal oxide coating including one or more oxides selected from the group consisting of an oxide of titanium, an oxide of zirconium and an oxide of hafnium.

21. The clamping arrangement as defined in claim 20, wherein said tungsten material includes at least 95 weight percent tungsten and one or more additives selected from the group consisting of at least about 0.5 weight percent of an oxide of thorium, at least about 0.5 weight percent of an oxide of lanthanum, and at least about 0.5 weight percent hafnium carbide.

22. The clamping arrangement as defined in claim 20, wherein said tungsten material includes at least about 10 weight percent rhenium.

23. The method as defined in claim 16, including the step of pressing said first and second articles together by at least one of said clamp during said step of applying heat.

24. The method as defined in claim 16, wherein said bond between said first and second articles is formed by a controlled bonding temperature and a controlled bonding pressure, a selection of said controlled bonding temperature and said controlled bonding pressure is at least partially based on a relationship of $Y=c-mX$, wherein Y is a ratio of said bonding pressure to an ultimate tensile strength of said first and second articles at a temperature of 60% of a melting temperature of said first and second articles, X is a ratio of said bonding temperature to said melting temperature of said first and second articles, c is about 1 to 1.4, and m is about 1 to 1.4.

25. The clamping arrangement as defined in claim 16, wherein at least a portion of an outer surface of said first clamp includes a metal oxide coating that is designed to contact said article, said metal oxide coating including one or more oxides selected from the group consisting of an oxide of titanium, an oxide of zirconium and an oxide of hafnium.

26. The clamping arrangement as defined in claim 16, wherein said tungsten material includes at least 95 weight percent tungsten and one or more additives selected from the group consisting of at least about 0.5 weight percent of an oxide of thorium, at least about 0.5 weight percent of an oxide of lanthanum, and at least about 0.5 weight percent hafnium carbide.

27. The clamping arrangement as defined in claim 16, wherein said tungsten material includes at least about 10 weight percent rhenium.

28. The method as defined in claim 16, including the step of forming an inert atmosphere at least partially at or near a region wherein said first and second articles are in contact during said step of applying heat.

29. The method as defined in claim 16, wherein said step of applying heat includes the use of a laser or electron beam.

* * * * *